(12) United States Patent
Inoue (10) Patent No.: US 10,441,475 B2
(45) Date of Patent: Oct. 15, 2019

(54) PLACEMENT DEVICE, PLACEMENT SYSTEM AND PLACEMENT METHOD

(71) Applicant: ZUIKO CORPORATION, Osaka (JP)

(72) Inventor: Daisuke Inoue, Osaka (JP)

(73) Assignee: Zuiko Corporation, Osaka (JP)

( * ) Notice: Subject to any disclaimer, the term of this patent is extended or adjusted under 35 U.S.C. 154(b) by 0 days.

(21) Appl. No.: 16/302,660

(22) PCT Filed: May 24, 2017

(86) PCT No.: PCT/JP2017/019377
§ 371 (c)(1),
(2) Date: Nov. 18, 2018

(87) PCT Pub. No.: WO2017/208932
PCT Pub. Date: Dec. 7, 2017

(65) Prior Publication Data
US 2019/0175423 A1    Jun. 13, 2019

(30) Foreign Application Priority Data

Jun. 1, 2016 (JP) .................. 2016-109757

(51) Int. Cl.
*A61F 13/15* (2006.01)
*B65G 47/84* (2006.01)

(52) U.S. Cl.
CPC ........ *A61F 13/15764* (2013.01); *A61F 13/15* (2013.01); *A61F 13/15756* (2013.01); *B65G 47/846* (2013.01)

(58) Field of Classification Search
CPC .. B65G 47/846; B65G 47/847; B65G 47/848; A61F 13/15; A61F 13/84;
(Continued)

(56) References Cited

U.S. PATENT DOCUMENTS 9,265,670 B2 *   2/2016   Shimada ................ A61F 13/49
9,433,538 B2 *   9/2016   Pagel ................ A61F 13/15723
(Continued)

FOREIGN PATENT DOCUMENTS

| JP | 2002-253606 A | 10/2002 |
|---|---|---|
| JP | 2011-25079 A | 2/2011 |
| JP | 2013-255624 A | 12/2013 |

OTHER PUBLICATIONS

International Search Report Issued in PCT/JP2017/019377 dated Aug. 15, 2017.

*Primary Examiner* — James R Bidwell
(74) *Attorney, Agent, or Firm* — Renner, Otto, Boisselle & Sklar, LLP (57) ABSTRACT

A placement device for arranging parts of a disposable worn article on the base material B, wherein: a first unit U1 includes first and third pads P1 and P3 capable of accelerating and decelerating; a second unit U2 includes second and fourth pads P2 and P4 capable of accelerating and decelerating; the first unit U1 includes separate servo motors M for rotating the first pad P1 and the third pad P3 about a common axis and does not include three or more servo motors M; and the second unit U2 includes separate servo motors M for rotating the second pad P2 and the fourth pad about a common axis and does not include three or more servo motors M.

9 Claims, 8 Drawing Sheets

(58) Field of Classification Search
CPC .......... A61F 13/15723; A61F 13/15756; A61F 13/15804; B32B 38/04; B32B 38/06; B32B 38/10; A61L 15/16
USPC ..... 198/459.2; 156/250, 252, 256, 259, 263, 156/264, 265
See application file for complete search history.

(56) References Cited

U.S. PATENT DOCUMENTS

| | | | |
|---|---|---|---|
| 9,498,386 B2* | 11/2016 | Darcey | A61F 13/15699 |
| 2002/0112939 A1* | 8/2002 | Sumi | A61F 13/15764 |
| | | | 198/377.08 |
| 2003/0066609 A1* | 4/2003 | Calvert | A61F 13/15772 |
| | | | 156/362 |
| 2004/0124068 A1* | 7/2004 | Berndtsson | G06K 19/07716 |
| | | | 198/608 |
| 2007/0142808 A1 | 6/2007 | Wada et al. | |
| 2013/0152360 A1* | 6/2013 | Schoultz | B65H 39/14 |
| | | | 29/428 |

* cited by examiner

PLACEMENT DEVICE, PLACEMENT SYSTEM AND PLACEMENT METHOD

TECHNICAL FIELD

The present invention relates to a placement device, a placement system and a placement method for placing parts on a base material of a disposable worn article.

BACKGROUND ART

With disposable worn articles, it is often the case that parts such as fastening members are attached to a base material, such as a continuous material, which is to be the worn article after being processed (the first patent document).

CITATION LIST

Patent Literature

[First Patent Document] JP2013-255624 A (front page)

With the conventional technique, a continuous sheet is severed into a plurality of parts, which are placed on a base material while the parts are spread apart from each other in the flow direction with a predetermined interval therebetween. In order to increase the interval between the parts to the predetermined interval, the placement device of the conventional technique uses a servo motor to rotate pads that pick up parts, and the rotation speed of the servo motor is changed for each revolution of the pads.

SUMMARY OF INVENTION

In order to increase the interval between parts, it is necessary to accelerate and decelerate the servo motor. This increases the load on the motor.

In order to solve the problem, it is possible to place three or more pads on a single rotation axis. However, this will require one servo motor for each pad that picks up a part. Therefore, placing three or more pads on a single rotation axis may possibly not only complicate the structure of the device but also lower the part placement precision.

It is an object of the present invention to provide a placement device, a placement system and a placement method, with which it is possible to reduce the load on the servo motor and to place parts on a base material with the interval therebetween spread wide using a simple configuration.

In one aspect, a placement device of the present invention is a placement device for placing parts of a disposable worn article on a base material B, the placement device including:

a base transfer device BT for carrying the base material B;
a part transfer unit UT for carrying a plurality of parts separated from each other; and
two or more re-pitch units each for intermittently picking up the plurality of parts from the part transfer unit UT and intermittently placing the plurality of parts on the base material B, wherein:

each of the two or more re-pitch units includes two pads, each of which picks up one of the plurality of parts, accelerates until placing the one picked-up part on the base material B, and decelerates after the placement;
each of the re-pitch units includes one servo motor M for rotating one of the two pads and another servo motor M for rotating another one of the two pads, and does not include three or more servo motors M (i.e., includes less than three servo motors); and
the two pads of each of the re-pitch units rotate about a common axis.

In another aspect, a placement device of the present invention is a placement device for placing parts of a disposable worn article on a base material B, the placement device including:

a base transfer device BT for carrying the base material B;
a part transfer unit UT for carrying a plurality of parts separated from each other;
a first unit U1 for intermittently picking up some parts (of the plurality of parts) from the part transfer unit UT and intermittently placing the some parts on the base material B; and
a second unit U2 for intermittently picking up other parts (of the plurality of parts) from the part transfer unit UT and intermittently placing the other parts on the base material B, wherein:

the first unit U1 includes a first pad P1 and a third pad P3, each of which picks up one of the plurality of parts, accelerates until placing the one picked-up part on the base material B, and decelerates after the placement of the one picked-up part;
the second unit U2 includes a second pad P2 and a fourth pad P4, each of which picks up another one of the plurality of parts, accelerates until placing the other picked-up part on the base material B, and decelerates after the placement of the other picked-up part;
the first unit U1 includes one servo motor M for rotating the first pad P1 and another servo motor M for rotating the third pad P3, and does not include three or more servo motors M (i.e., includes less than three servo motors), wherein the first pad P1 and the third pad P3 rotate about a common axis; and
the second unit U2 includes one servo motor M for rotating the second pad P2 and another servo motor M for rotating the fourth pad P4, and does not include three or more servo motors M (i.e., includes less than three servo motors), wherein the second pad P2 and the fourth pad P4 rotate about a common axis.

Where there are two units (first and second units) for intermittently picking up parts from the part transfer unit UT and intermittently placing the parts on the base material B, the placement device includes:

a base transfer device BT for carrying the base material B;
a part transfer unit UT for carrying a plurality of parts separated from each other;
a first unit U1 for intermittently picking up some of the plurality of parts from the part transfer unit UT and intermittently placing the some of the plurality of parts on the base material B; and
a second unit U2 for intermittently picking up, at a position on the part transfer unit UT downstream of the first unit U1, the remaining parts that have not been picked up by the first unit U1 from the part transfer unit UT and intermittently placing the remaining parts on the base material B at a position on the base transfer device BT upstream of the first unit U1, wherein:

the first unit U1 includes a first pad P1 for picking up an $(i+1)^{th}$ one (i is 0 or a multiple of 4) of the plurality of parts, accelerates until placing the picked-up $(i+1)^{th}$ part on the base material B, and decelerates after the placement of the picked-up $(i+1)^{th}$ part;
the second unit U2 includes a second pad P2 for picking up a $(j+2)^{th}$ one (j is 0 or a multiple of 4) of the plurality of parts, accelerates until placing the picked-up $(j+2)^{th}$ part on the base material B, and decelerates after the placement of the picked-up $(j+2)^{th}$ part;

the first unit U1 includes a third pad P3 for picking up an $(i+3)^{th}$ one of the plurality of parts, accelerates until placing the picked-up $(i+3)^{th}$ part on the base material B, and decelerates after the placement of the picked-up $(i+3)^{th}$ part;

the second unit U2 includes a fourth pad P4 for picking up a $(j+4)^{th}$ one of the plurality of parts, accelerates until placing the picked-up $(j+4)^{th}$ part on the base material B, and decelerates after the placement of the picked-up $(j+4)^{th}$ part;

the first, second, third and fourth pads P1 to P4 are placed at the same position in a width direction D2 perpendicular to a carrying direction D1 of the plurality of parts;

the first unit U1 includes one servo motor M for rotating the first pad P1 and another servo motor M for rotating the third pad P3, and does not include three or more servo motors M (i.e., includes less than three servo motors), wherein the first pad P1 and the third pad P3 rotate about a common axis; and the second unit U2 includes one servo motor M for rotating the second pad P2 and another servo motor M for rotating the fourth pad P4, and does not include three or more servo motors M (i.e., includes less than three servo motors), wherein the second pad P2 and the fourth pad P4 rotate about a common axis.

In order to place the parts by using the placement device, each of the first, second, third and fourth pads P1 to P4 picks up ones of the plurality of parts and places the ones on the base material B with an interval between the ones, the interval accounting for a number of positions where other parts of the plurality of parts are supposed to be placed, and the number of the other parts being one less than the total number of the pads P1 to P4.

Where there are two units (first and second units) for intermittently picking up parts from the part transfer unit UT and intermittently placing the parts on the base material B, the placement method is more specifically a method, wherein:

the base transfer device BT transfers the base material B;
the part transfer unit UT transfers the plurality of parts;
the first pad P1 repeats a step of picking up the $(i+1)^{th}$ part (i is 0 or a multiple of 4), accelerating until placing the picked-up $(i+1)^{th}$ part on the base material B, and decelerating after the placement of the picked-up $(i+1)^{th}$ part;

the second pad P2 repeats a step of picking up the $(j+2)^{th}$ part (j is 0 or a multiple of 4), accelerating until placing the picked-up $(j+2)^{th}$ part on the base material B, and decelerating after the placement of the picked-up $(j+2)^{th}$ part;

the third pad P3 repeats a step of picking up the $(i+3)^{th}$ part, accelerating until placing the picked-up $(i+3)^{th}$ part on the base material B, and decelerating after the placement of the picked-up $(i+3)^{th}$ part;

the fourth pad P4 repeats a step of picking up the $(j+4)^{th}$ part, accelerating until placing the picked-up $(j+4)^{th}$ part on the base material B, and decelerating after the placement of the picked-up $(j+4)^{th}$ part; and as a result of the first, second, third and fourth pads repeating their steps, the first, second, third and fourth pads P1 to P4 repeatedly place the $(i+1)^{th}$, $(j+2)^{th}$, $(i+3)^{th}$ and $(j+4)^{th}$ parts on the base material B in the order of the $(i+1)^{th}$, $(j+2)^{th}$, $(i+3)^{th}$ and $(j+4)^{th}$ parts, so that each product has one of the $(i+1)^{th}$, $(j+2)^{th}$, $(i+3)^{th}$ and $(j+4)^{th}$ parts placed thereon.

According to the present invention, each of the first and second units (re-pitch units) rotates a pair of pads placed around a single common axis by means of a pair of servo motors. That is, each unit only needs to be provided with two pairs of pads and servo motors, but does not need to be provided with three pairs. Thus, the configuration of the placement device is simplified.

That is, the re-pitch unit includes separate servo motors for rotating pads about a single common axis (one servo motor for each pad), and does not include three or more servo motors. With each servo motor, this simplifies the structure for rotating the pad.

Particularly, each of the first and second units (re-pitch units) is provided with two servo motors and two pads, and one placement device includes twice as many servo motors and pads as the number of units. For example, where the number of units is two, one placement device includes four servo motors and four pads. Therefore, in such a case, for every four worn articles, each pad only needs to place one part on the base material B, which is transferred by the base transfer device BT. Thus, the speed or the acceleration of each pad is low, and the load of each servo motor is low.

For example, for two units, a total of four or more pads may be provided (two servo motors are provided for each unit). For example, for three re-pitch units, a total of six or more pads may be provided (two servo motors are provided for each unit). Thus, it is possible to lower the load of the servo motor, and to place parts on the base material while the interval between the parts is widened.

Where two parts that are spaced apart from each other in the width direction of the base material perpendicular to the flow direction are placed on the opposite side portions of the base material, a pair of placement devices are provided.

That is, in such a case, a placement device A1, which is one of the placement devices, and a placement device A2, which is the other one of the placement devices, are arranged so as to be spaced apart from each other in the width direction D2 of the base material B perpendicular to the carrying direction D1 thereof so that the plurality of parts can be placed on the first and second edge portions B1 and B2, with respect to the width direction D2, of the base material B. That is, the placement device A1 places parts on the first edge portion B1, and the placement device A2 places parts on the second edge portion B2.

In such a case, the placement device A1 can place parts on the first edge portion B1 of the base material, while the placement device A2 can place parts on the second edge portion B2 of the base material.

DESCRIPTION OF EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Before describing the placement device, etc., according to an embodiment of the present invention, an example of a worn article will be described with reference to the drawings.

Figure 1:
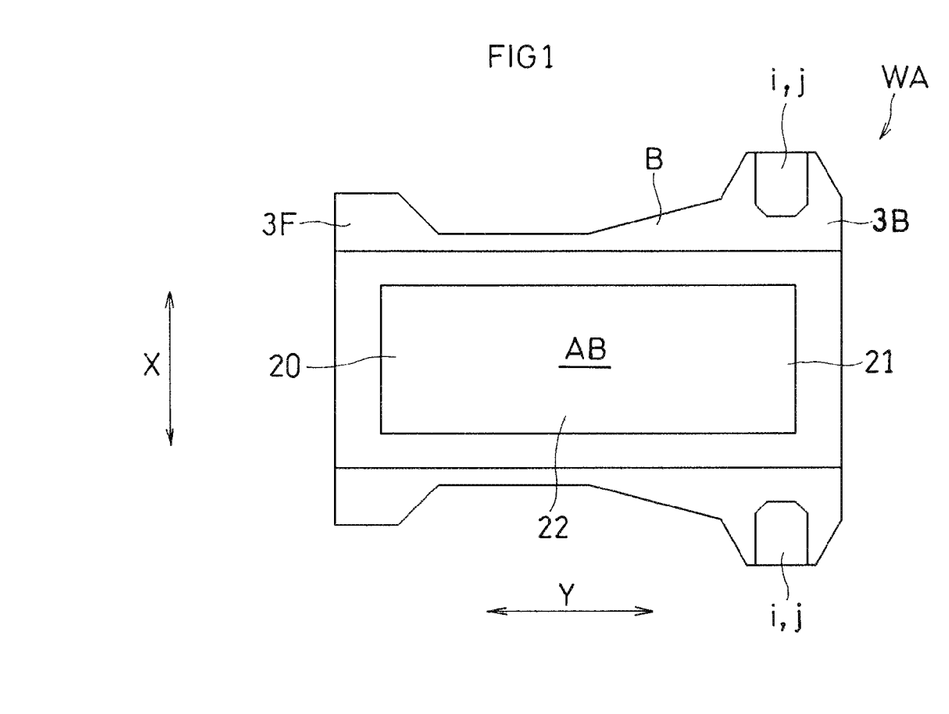
FIG. 1 is a developed view showing an example of a worn article according to the present invention.

As shown in FIG. 1, the worn article WA includes an absorbent body AB and the base material B such as an external non-woven fabric. The absorbent body AB includes a front portion 20, a back portion 21 and a crotch portion 22. The front portion 20 extends in the girth direction X, covering the front torso (the front portion of the torso) of the wearer. The back portion 21 extends in the girth direction X, covering the rear torso (the rear portion of the torso) of the wearer. The crotch portion 22 covers the crotch of the wearer between the front portion 20 and the back portion 21.

The crotch portion 22 is continuous with the front portion 20 and the back portion 21 in the vertical direction (longitudinal direction) Y perpendicular to the girth direction X, and the absorbent body AB is elongated in the vertical direction Y. The present worn article is worn while the crotch portion 22 is folded in two along a virtual line that is parallel to the girth direction X.

Although not shown in the figures, an absorbent core is provided on the absorbent body AB. The absorbent core absorbs body fluid. The absorbent core is sandwiched between the top sheet and the back sheet (not shown) of the absorbent body AB. These sheets and the absorbent core are layered together. A cuff may be provided on the top sheet.

Elastic members for waist and hips (not shown) may be provided on front and rear girth portions 3F and 3B that respectively cover the front and rear torso portions of the wearer when worn.

The elastic members are for fitting the girth portions to the wearer. For example, a plurality of rubber threads may be placed or a strip-shaped stretchable member may be placed as the elastic members.

When the worn article is a diaper, parts i and j such as tape materials with a fastening agent applied thereon may be secured at the opposite ends of the rear girth portion 3B in the girth direction X. Instead of the tape material, the parts i and j may be a male touch fastener (not shown) secured on the rear girth portion as a fastening member, and a female touch fastener secured on the non-skin-contact surface (the surface that does not face the skin of the wearer when worn) of the front girth portion.

Next, a device and a system for placing the parts i and j on the base material B of the worn article WA will be described with reference to FIG. 5 to FIG. 8.

Figure 2:
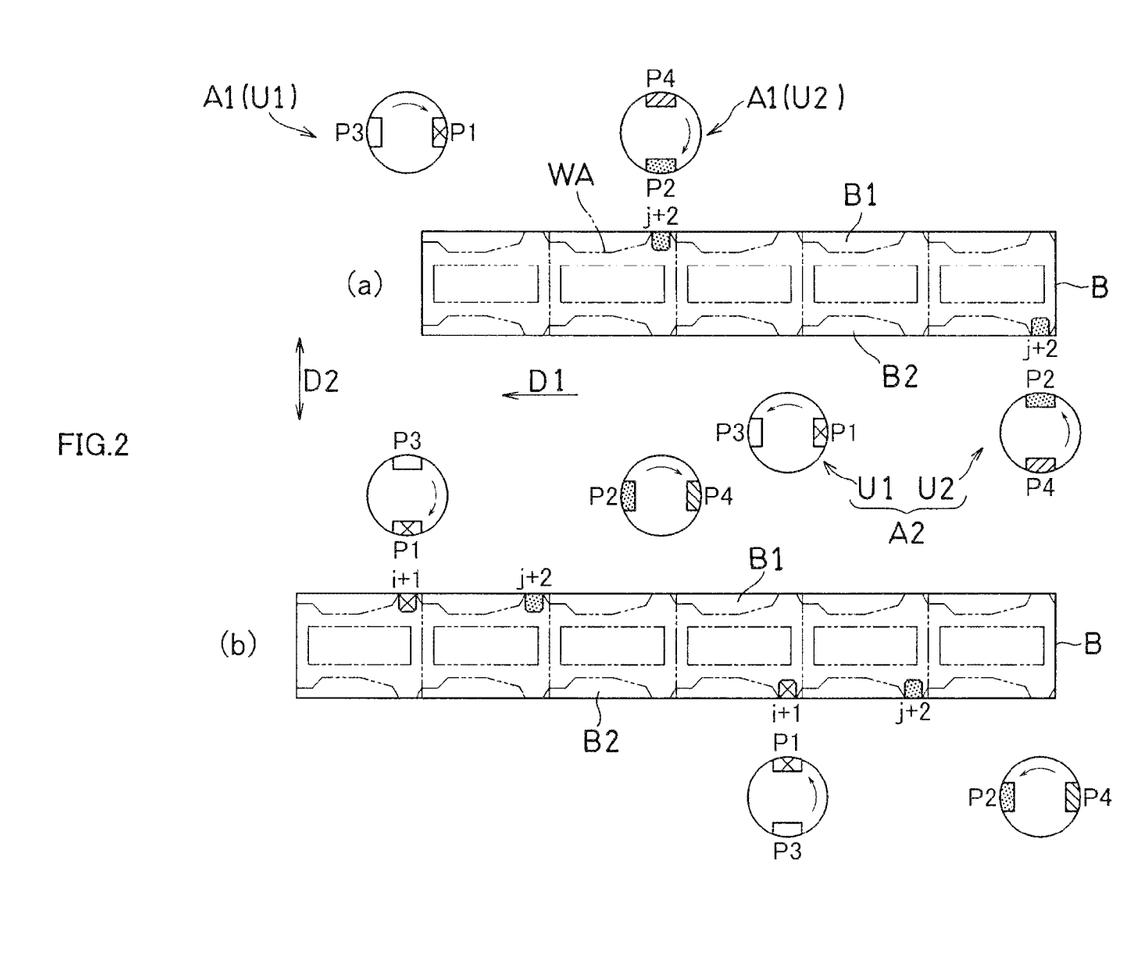
FIG. 2 is a process view showing a placement method according to an embodiment of the present invention.
Figure 5:
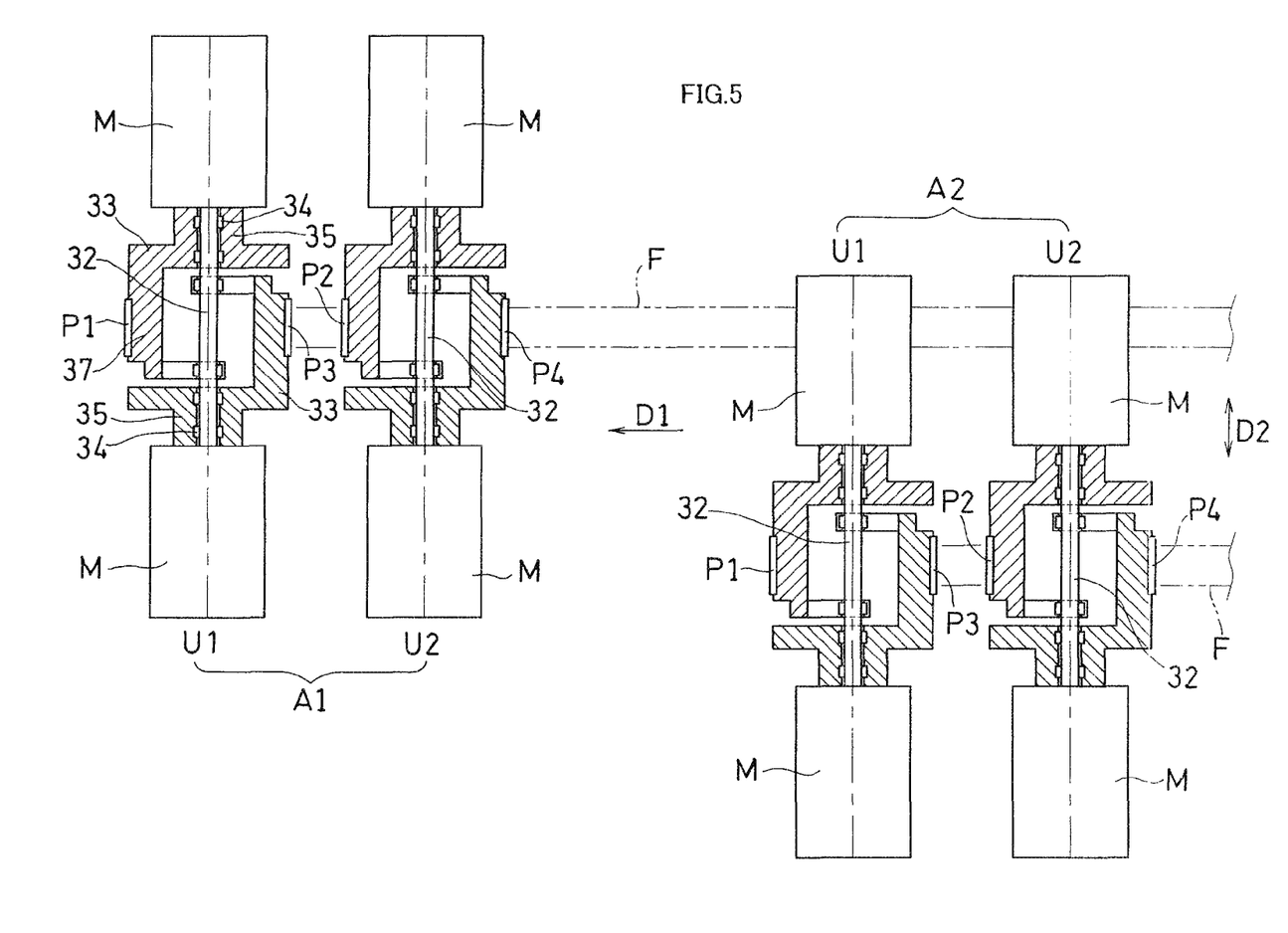
FIG. 5 is a partially cut-away plan view showing a rotor of first and second units of a placement system of the present invention.
Figure 6:
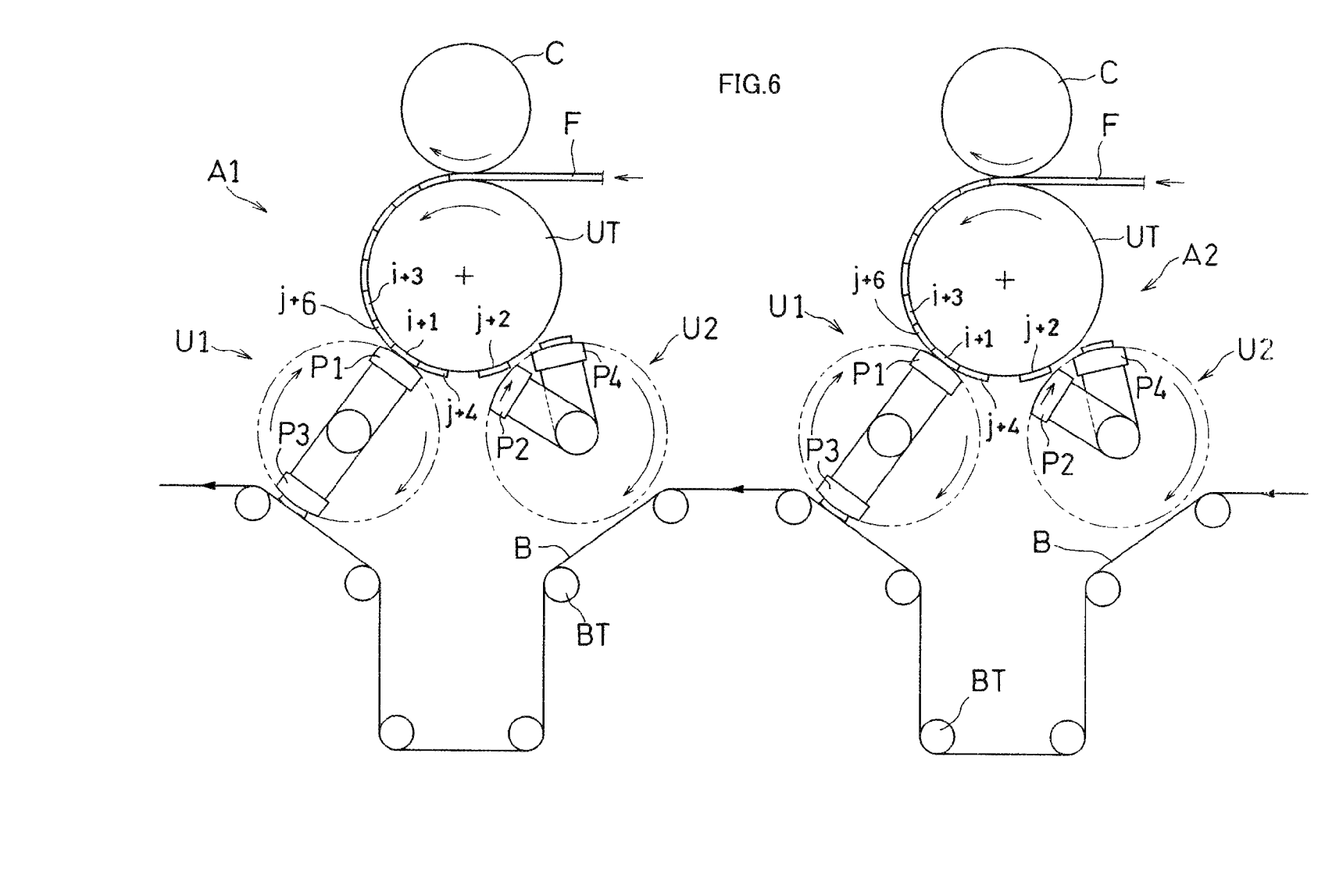
FIG. 6 is a layout diagram showing the placement system of the present invention.

The present placement system of FIG. 6 includes first and second placement devices A1 and A2. The first placement device A1 and the second placement device A2 respectively place the parts i and j on first and second edge portions B1 and B2, with respect to the width direction D2 perpendicular to the carrying direction D1, of the base material B, as shown in FIG. 2. Therefore, the first placement device A1 and the second placement device A2 are spaced apart from each other in the width direction D2, as shown in FIG. 5.

Note that F in FIG. 5 denotes a continuous material of the parts.

As shown in FIG. 6, the first and second placement devices A1 and A2 have the same structure in terms of mechanical structure. Therefore, the structure and the operation of only the first placement device A1 will be described.

Figure 7:
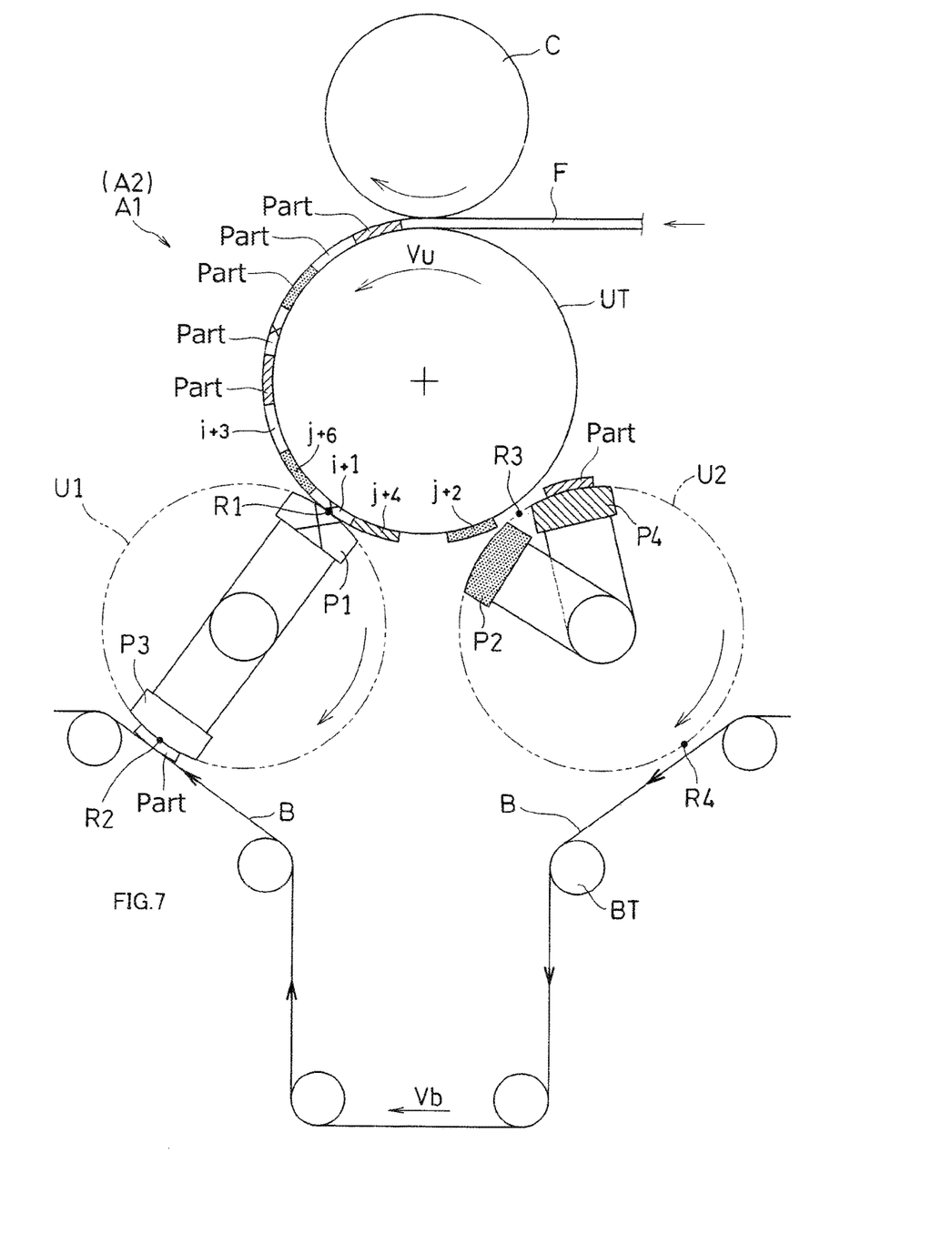
FIG. 7 is a schematic side view showing a placement device of the present invention.

In FIG. 7, the first placement device A1 includes a base transfer device BT for transferring the base material B. The base material B is a continuous material to be the worn article WA of FIG. 2, for example.

The first placement device A1 of FIG. 7 also includes the part transfer unit UT for transferring parts separated from each other, and a cutter drum C. In this example, the part transfer unit UT is an anvil roller. The cutter drum C successively severs the continuous material F of the parts wound around and carried on the part transfer unit UT into individual parts i and j. The part transfer unit UT transfers, along the drum, the parts i and j that have been severed and separated from each other.

The first placement device A1 includes first and second (re-pitch) units U1 and U2.

The first unit U1 includes first and third pads P1 and P3. On the other hand, the second unit U2 includes second and fourth pads P2 and P4.

The first pad P1 and the third pad P3 of the first unit U1 intermittently pick up, at the pick-up position R1, some of the plurality of parts from the part transfer unit UT. Then, at the hand-over position R2, the first pad P1 and the third pad P3 intermittently place some of the plurality of parts on the base material B.

The second pad P2 and the fourth pad P4 of the second unit U2 intermittently pick up, at another pick-up position R3 on the part transfer unit UT downstream of the first unit U1, the remaining parts that have not been picked up by the first unit U1 from the part transfer unit UT, and the second pad P2 and the fourth pad P4 intermittently place the parts on the base material B at another hand-over position R4 on the base transfer device BT upstream of the first unit U1.

As shown in FIG. 5, the first, second, third and fourth pads P1 to P4 of the first and second placement devices A1 and A2 are placed at the same position in the width direction D2 perpendicular to the carrying direction D1 of the parts.

In FIG. 7, the first pad P1 picks up the $(i+1)^{th}$ one (i is 0 or a multiple of 4) of the plurality of parts at the pick-up position R1, accelerates until placing the part on the base material B at the hand-over position R2, and decelerates after the placement.

The second pad P2 picks up the $(j+2)^{th}$ one (j is 0 or a multiple of 4) of the plurality of parts at the pick-up position R3, accelerates until placing the part on the base material B at the hand-over position R4, and decelerates after the placement.

The third pad P3 picks up the $(i+3)^{th}$ one of the plurality of parts at the pick-up position R1, accelerates until placing the part on the base material B at the hand-over position R2, and decelerates after the placement.

The fourth pad P4 picks up the $(j+4)^{th}$ one of the plurality of parts at the pick-up position R3, accelerates until placing the part on the base material B at the hand-over position R4, and decelerates after the placement.

Note that pads for picking up parts and parts picked up thereby are marked with dotting, and the like, so as to make conspicuous the correspondence therebetween.

As shown in FIG. 5, the first unit U1 includes separate servo motors M for rotating the first pad P1 and the third pad P3 about a common axis, and does not include three or more servo motors M.

The second unit U2 includes separate servo motors M for rotating the second pad P2 and the fourth pad P4 about a common axis, and does not include three or more servo motors M.

While each pad of the first unit U1 picks up and carries a group of parts i and each pad of the second unit U2 picks up and carries a group of parts j next to the parts i, as shown in FIG. 7, the first unit U1 and the second unit U2 have the same structure in terms of mechanical structure. Therefore, the structure and the operation of only the first unit U1 will be described. The first unit U1 is a variable-speed roller to be described below.

In FIG. 7, the first or third pad P1 or P3 of the first unit U1, which is a variable-speed roller, picks up a part i from the part transfer unit UT at the pick-up position R1 at which the first or third pad P1 or P3 contacts the transfer unit UT with the part i therebetween.

Then, the first and third pads P1 and P3 place a part i on the base material B carried by the base transfer device BT at the hand-over position R2 at which the first or third pad P1 or P3 contacts the base material B with the part i therebetween. As shown in FIG. 2, the base material B is arranged so that the longitudinal direction Y of the worn articles extends along the carrying direction D1 and the worn articles are continuous with each other in the carrying direction D1.

Figure 8:
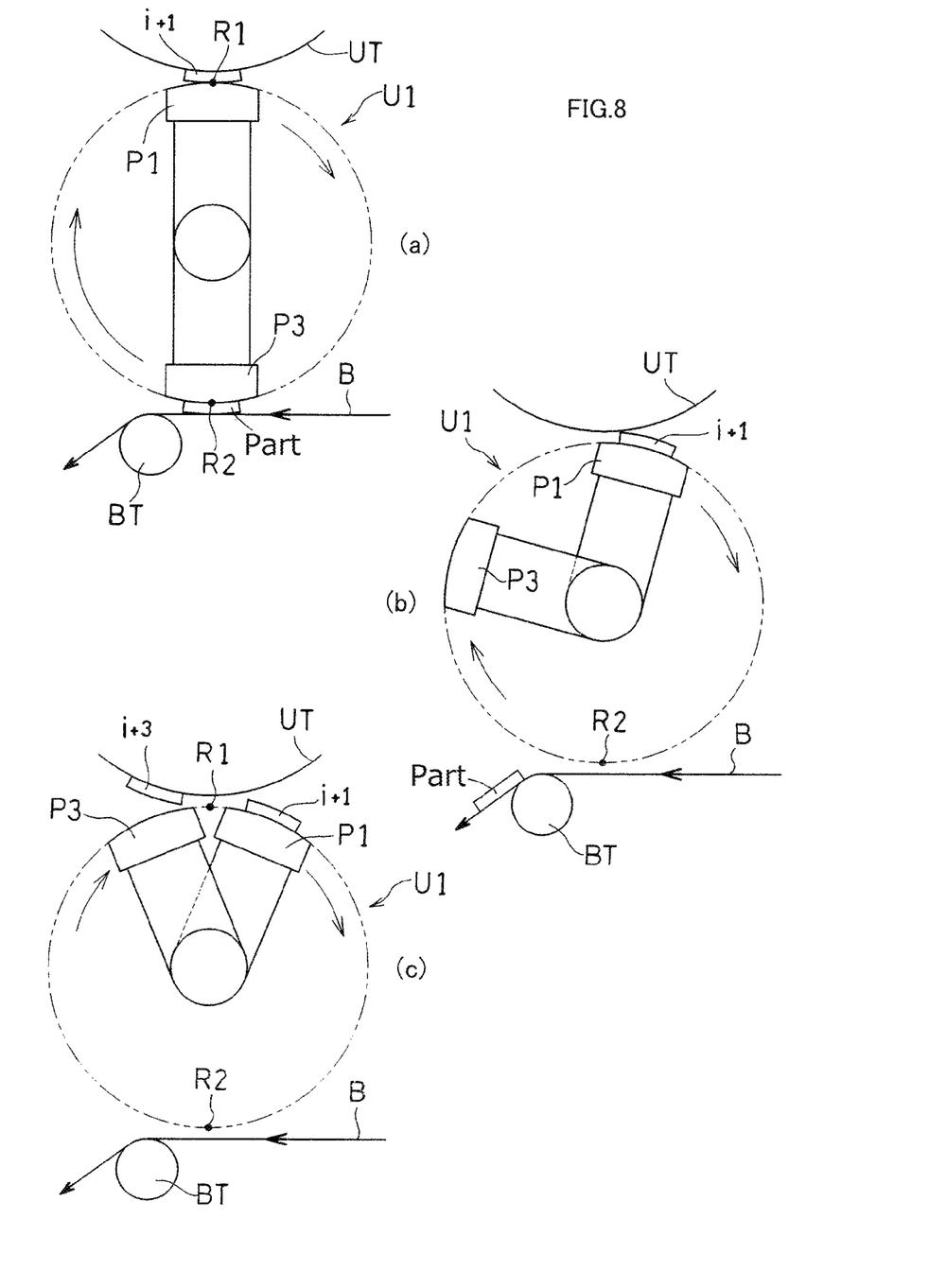
FIG. 8 is a conceptual view showing the operation of the rotor.

The speed Vb of the base transfer device BT of FIG. 7 is greater than the speed Vu of the part transfer unit UT. Therefore, each servo motor M of FIG. 5 accelerates the pad P1 (P3) from the speed Vu to the speed Vb over the section from the pick-up position R1 to the hand-over position R2, as shown in FIG. 8.

The part i is placed on the base material B from the pad P1 (P3) at the hand-over position R2. After the placement, the pad P1 (P3) decelerates from the speed Vb to the speed Vu and picks up the part i again at the pick-up position R1.

This further increases the distance between the part i on one first pad P1 and the following part i on the other third pad P3. As a result, the pitch between the parts of FIG. 7 increases four times, for example.

Next, the detailed structure of the first unit U1 of FIG. 5 will be described.

The first unit U1 includes one support shaft 32 elongated in the axial direction, and a pair of rotors 33 that rotate about the support shaft 32, for example.

Each rotor 33 includes first and second born sections 35 supported at the respective end portions of the support shaft 32 via bearings 34. Thus, the pair of rotors 33 are allowed to rotate about the support shaft 32 without being restrained by each other.

A pad base 37 is continuous with the first (second) born section 35, and the first pad P1 (the third pad P3) is placed on the surface of the pad base 37. The first and third pads P1 and P3 may be arc-shaped, for example.

The servo motor M is linked to each born section 35. Therefore, the first and third pads P1 and P3 are each accelerated or decelerated as the rotation speed of the corresponding servo motor M changes.

Note that FIG. 6 to FIG. 8 are diagrams schematically showing the placement device, and sizes and shapes of the pads, etc., in these figures are different from those of FIG. 5.

Next, an example of how the first and third pads P1 and P3 are operated by changing the speed of the pair of servo motors M will be described. The operation of the servo motor M is controlled by a control device (not shown).

As shown in FIGS. 8(a) to 8(c), the speeds of the pair of pads P1 and P3 change periodically as each servo motor M accelerates at least once and decelerates at least once during one revolution of each pad.

That is, the speed of each pad P1, P3 is equal to the low speed Vu (the speed of the part transfer unit UT) at or around the pick-up position R1, at which the pad contacts the part transfer unit UT with a part therebetween. On the other hand, the speed of each pad P1, P3 is equal to the high speed Vb (the speed of the base transfer device BT) at or around the hand-over position R2, at which the pad contacts the base material B with a part therebetween.

Between at or around the pick-up position R1 and at or around the hand-over position R2, the pad P1, P3 rotates at a speed that is between the speed Vb and the speed Vu, thereby increasing the distance between the preceding part and the following part, as well known in the art.

In other words, while the pad P1, P3 moves from the pick-up position R1 and returns back to the pick-up position R1 after one revolution, the pad P1, P3 (i) moves at the low speed Vu at or around the pick-up position R1, (ii) accelerates to a speed that is greater than the speed Vu, and (iii) accelerates to a speed that is equal to the high speed Vb after entering the vicinity of the hand-over position R2.

When the pad P1, P3 moves past the vicinity of the hand-over position R2 after placing a part on the base material B at the hand-over position R2, the pad P1, P3 decelerates to a speed that is less than the high speed Vb. Then, after entering the vicinity of the pick-up position R1, the pads P1, P3 further decelerates to the low speed Vu.

Next, an example of the method for placing parts will be described.

Figure 4:
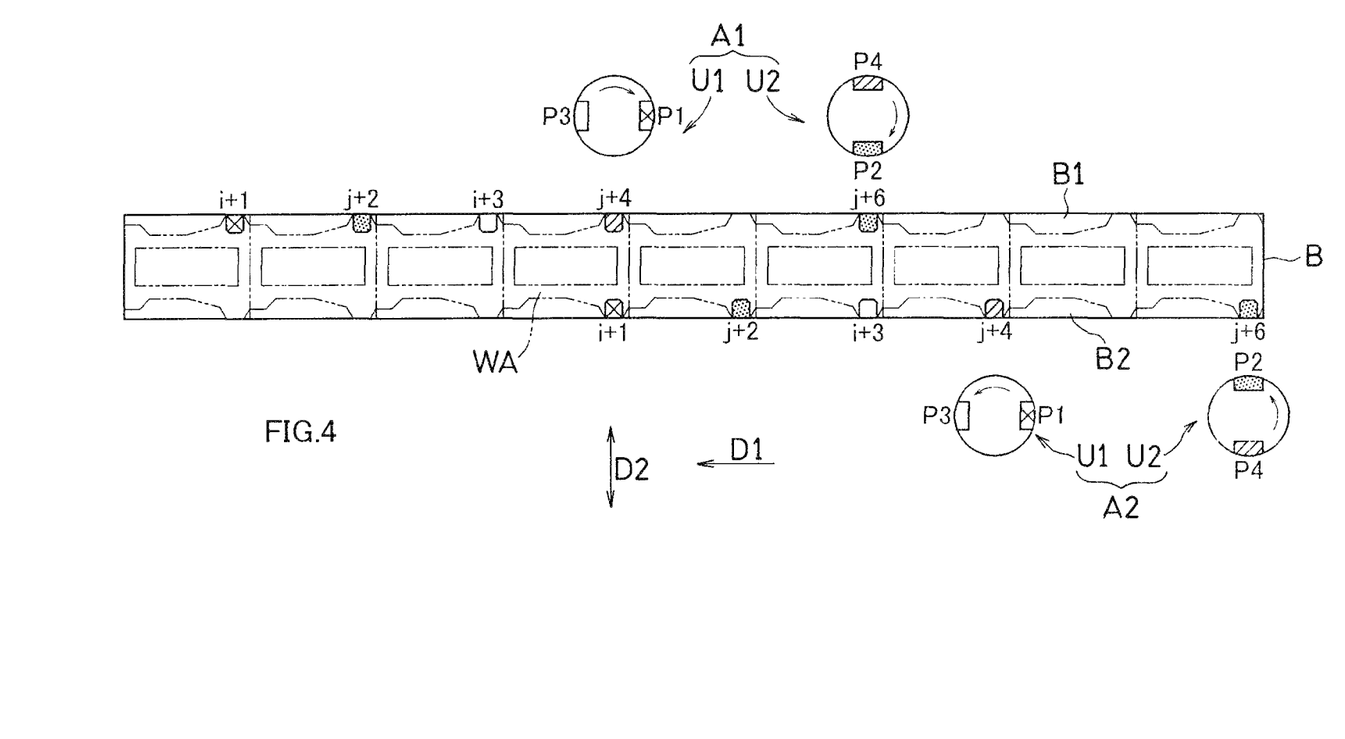
FIG. 4 is a process view showing a placement method according to an embodiment of the present invention.

A plurality of parts are placed on the first edge portion B1 and on the second edge portion B2 of the base material B of FIG. 4 by substantially the same method. Thus, a method for placing parts i+1, j+2, i+3 and j+4 on the first edge portion B1 of the base material B will be described.

In FIG. 6, the base transfer device BT transfers the base material B. On the other hand, two part transfer units UT transfer the parts.

A method for placing parts on the first edge portion B1 of the base material B by the first placement device A1 will now be described.

The second pad P2 of FIG. 7 picks up the (j+2)$^{th}$ part (j is 0 or a multiple of 4) at the pick-up position R3, accelerates until placing the part on the base material B, i.e., up to the hand-over position R4, and decelerates after the placement. Thus, the part j+2 is placed on the first edge portion B1 of the base material B of FIG. 2(a).

The first pad P1 of FIG. 7 picks up the (i+1)$^{th}$ part (i is 0 or a multiple of 4) at another pick-up position R1 on the part transfer unit UT upstream of the pick-up position R3, accelerates until placing the part on the base material B, i.e., up to another hand-over position R2 on the base transfer device BT downstream of the hand-over position R4, and decelerates after the placement. Thus, along the first edge portion B1 of the base material B of FIG. 2(b), the part i+1 is placed downstream of the part j+2 in the carrying direction D1.

The fourth pad P4 of FIG. 7 picks up the (j+4)$^{th}$ part at the pick-up position R3, accelerates until placing the part on the base material B, i.e., up to the hand-over position R4, and decelerates after the placement. Thus, along the first edge portion B1 of the base material B of FIG. 3(a), the part j+4 is placed upstream of the part j+2 in the carrying direction D1. The interval between the part j+2 and the part j+4 in the carrying direction D1 is set to be twice the interval between the part i+1 and the part j+2.

The third pad P3 of FIG. 7 picks up the (i+3)$^{th}$ part at the pick-up position R1, accelerates until placing the part on the base material B, i.e., up to the hand-over position R2, and decelerates after the placement. Thus, along the first edge portion B1 of the base material B of FIG. 3(b), the part i+3 is placed between the part j+2 and the part j+4.

Thus, the four parts i+1, j+2, i+3 and j+4 are placed, intermittently along the first edge portion B1 of the base material B with one part placed on each worn article unit, in this order from downstream to upstream in the carrying direction D1 of the base material B.

By repeating these steps, the first, second, third and fourth pads P1 to P4 repeatedly place the $(i+1)^{th}$, $(j+2)^{th}$, $(i+3)^{th}$, and $(j+4)^{th}$ parts in this order on the base material B, thereby placing one part on each product.

That is, the $j+6^{th}$ part of FIG. 7, which is four parts behind the $j+2^{th}$ part, is picked up by the second pad P2 at the pick-up position R3. Then, this part is placed at the hand-over position R4. Thus, the part j+6 is placed on the first edge portion B1 of the base material B as shown in FIG. 4.

Figure 3:
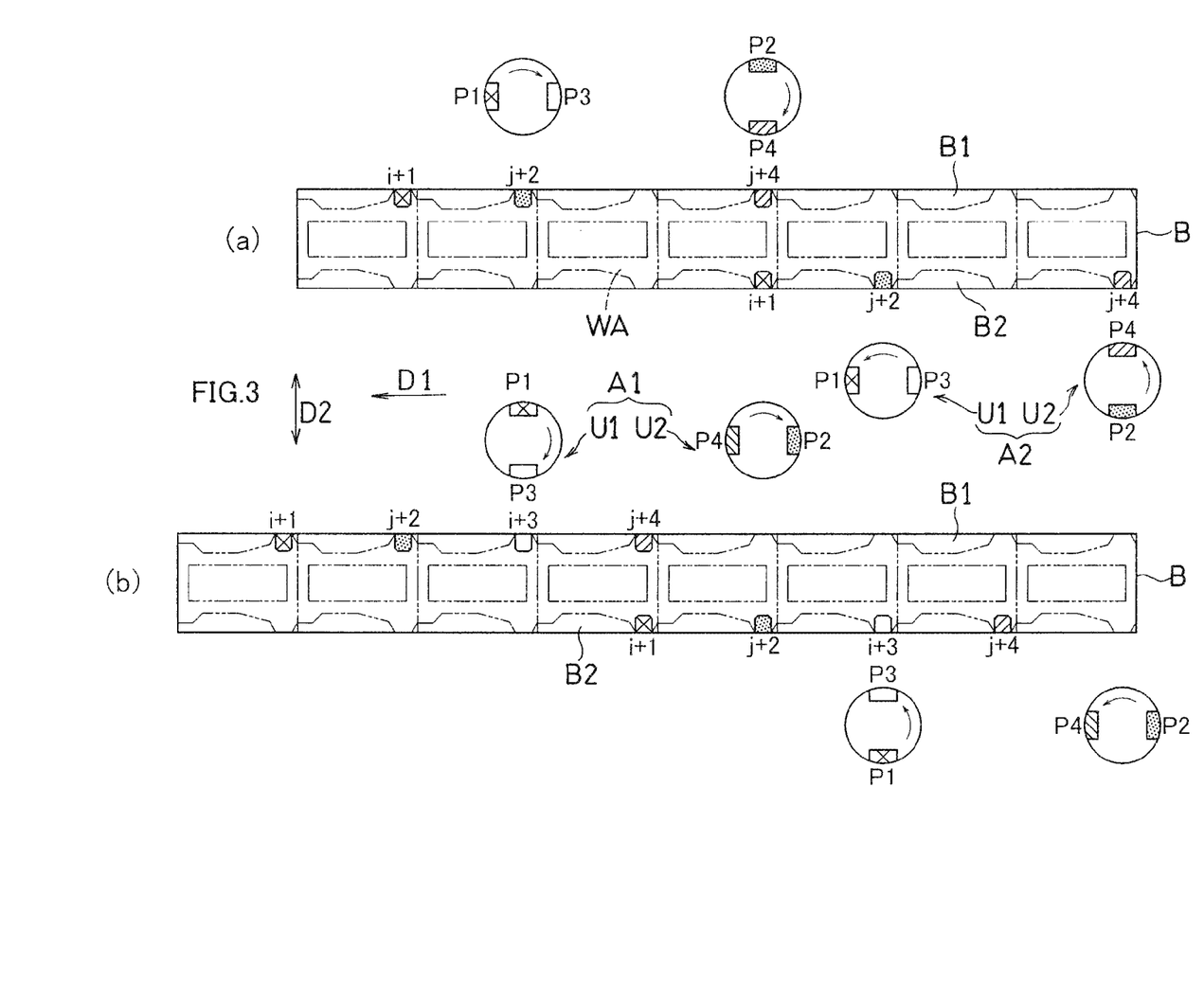
FIG. 3 is a process view showing a placement method according to an embodiment of the present invention.

Using substantially the same method as the method by which the first placement device A1 of FIG. 6 places parts on the first edge portion B1 of the base material B of FIG. 3, the second placement device A2 of FIG. 6 places parts on the second edge portion B2 of the base material B, as shown in FIG. 2, FIG. 3 and FIG. 4. Thus, parts are attached to the base material B with one part attached to each worn article. Note that the base material B is cut into worn article units, thereby producing the worn article WA of FIG. 1.

In the embodiment described above, four pads are provided for each placement device. Each of the first, second, third and fourth pads P1 to P4 places parts on the base material B with an interval between the parts placed by the same pad. The interval accounts for a number (three) of predetermined positions on the base material B at which parts are supposed to be placed. The number of predetermined positions is one less than the total number (four) of the pads P1 to P4. That is, as shown in FIG. 4, for example, the second pad P2 gives an interval between the part j+2 and the part j+6 placed on the base material B such that three parts, i.e., the part i+3, the part j+4 and the part i+5 (which have not yet been placed in FIG. 4), can be placed between the part j+2 and the part j+6. Three worn articles WA are formed between the worn article WA on which the part j+2 is placed and the worn article WA on which the part j+6 is placed.

In each placement device of the present invention, the number of (re-pitch) units each including two pads may be three or more. For example, where the number of (re-pitch) units is three, the number of pads is six. Each of the six pads places parts on the base material B with an interval therebetween that accounts for a number (five) of predetermined positions on the base material B at which parts are supposed to be placed that is one less than the total number (six) of the pads.

While preferred embodiments have been described above with reference to the drawings, various obvious changes and modifications will readily occur to those skilled in the art upon reading the present specification.

For example, parts do not have to be fastening members, but may be any other parts, such as strip-shaped stretchable sheets, or the like. In such a case, one stretchable sheet is provided for the rear girth portion of each worn article. Therefore, there is no need for the second placement device A2 of FIG. 6.

Although the parts on the part transfer unit UT before being picked up by the pads of FIG. 7 are adjacent to each other, they may be separated from each other while on the part transfer unit UT.

The base material to which parts are attached may be separated into a plurality of body portions.

Another type of a transfer means may be used to transfer a non-continuous base material.

Thus, such changes and modifications are deemed to fall within the scope of the present invention, which is defined by the appended claims.

INDUSTRIAL APPLICABILITY

The present invention is applicable to a placement method, a placement device, etc., for disposable worn articles.

REFERENCE SIGNS LIST

A1, A2: Placement device
B: Base material, BT: Base transfer device, B1: First side portion, B2: Second side portion
C: Cutter drum
D1: Carrying direction, D2: Width direction
F: Continuous material
UT: Part transfer unit, U1: First unit (re-pitch unit), U2: Second unit (re-pitch unit)
P1 to P4: First to fourth pads
M: Servo motor

The invention claimed is:

1. A placement device for placing parts of a disposable worn article on a base material, the placement device comprising:
   a base transfer device for carrying the base material;
   a part transfer unit for carrying a plurality of parts separated from each other; and
   two or more re-pitch units for intermittently picking up the plurality of parts from the part transfer unit and intermittently placing the plurality of parts on the base material, wherein:
   each of the two or more re-pitch units includes two pads, each of which picks up one of the plurality of parts, accelerates until placing the one on the base material, and decelerates after the placement;
   each of the re-pitch units includes one servo motor for rotating one of the two pads and another servo motor for rotating another one of the two pads, and does not include three or more servo motors; and
   the two pads of each of the re-pitch units rotate about a common axis.

2. A placement system comprising a pair of the placement devices according to claim 1, wherein:
   a placement device, which is one of the placement devices, and a placement device, which is another one of the placement devices, are arranged so as to be spaced apart from each other in a width direction of the base material perpendicular to a carrying direction thereof so that the plurality of parts are capable of being placed on a first edge portion and a second edge portion, with respect to the width direction, of the base material.

3. A placement device for placing parts of a disposable worn article on a base material, the placement device comprising:
   a base transfer device for carrying the base material;
   a part transfer unit for carrying a plurality of parts separated from each other;
   a first unit for intermittently picking up the plurality of parts from the part transfer unit and intermittently placing the plurality of parts on the base material; and a second unit for intermittently picking up the plurality of parts from the part transfer unit and intermittently placing the plurality of parts on the base material, wherein:

the first unit includes a first pad and a third pad, each of which picks up one of the plurality of parts, accelerates until placing the one on the base material, and decelerates after the placement of the one;

the second unit includes a second pad and a fourth pad, each of which picks up another one of the plurality of parts, accelerates until placing the other one on the base material, and decelerates after the placement of the other one;

the first unit includes one servo motor for rotating the first pad and another servo motor for rotating the third pad, and does not include three or more servo motors, wherein the first pad and the third pad rotate about a common axis; and the second unit includes one servo motor for rotating the second pad and another servo motor for rotating the fourth pad, and does not include three or more servo motors, wherein the second pad and the fourth pad rotate about a common axis.

4. A placement method using the placement device according to claim 3, wherein:

each of the first, second, third and fourth pads picks up ones of the plurality of parts and places the ones on the base material with an interval between the ones, the interval accounting for a number of positions where other parts of the plurality of parts are supposed to be placed, and the number of the other parts being one less than the total number of the pads.

5. A placement system comprising a pair of the placement devices according to claim 3, wherein:

a placement device, which is one of the placement devices, and a placement device, which is another one of the placement devices, are arranged so as to be spaced apart from each other in a width direction of the base material perpendicular to a carrying direction thereof so that the plurality of parts are capable of being placed on a first edge portion and a second edge portion, with respect to the width direction, of the base material.

6. A placement device for placing parts of a disposable worn article on a base material, the placement device comprising:

a base transfer device for carrying the base material;

a part transfer unit for carrying a plurality of parts separated from each other;

a first unit for intermittently picking up some of the plurality of parts from the part transfer unit and intermittently placing the some of the plurality of parts on the base material; and a second unit for intermittently picking up, at a position on the part transfer unit downstream of the first unit, remaining parts that have not been picked up by the first unit from the part transfer unit and intermittently placing the remaining parts on the base material at a position on the base transfer device upstream of the first unit, wherein:

the first unit includes a first pad for picking up an $(i+1)^{th}$ one (i is 0 or a multiple of 4) of the plurality of parts, accelerates until placing the $(i+1)^{th}$ one on the base material, and decelerates after the placement of the $(i+1)^{th}$ one;

the second unit includes a second pad for picking up a $(j+2)^{th}$ one (j is 0 or a multiple of 4) of the plurality of parts, accelerates until placing the $(j+2)^{th}$ one on the base material, and decelerates after the placement of the $(j+2)^{th}$ one;

the first unit includes a third pad n for picking up an $(i+3)^{th}$ one of the plurality of parts, accelerates until placing the $(i+3)^{th}$ one on the base material, and decelerates after the placement of the $(i+3)^{th}$ one;

the second unit includes a fourth pad for picking up a $(j+4)^{th}$ one of the plurality of parts, accelerates until placing the $(j+4)^{th}$ one on the base material, and decelerates after the placement of the $(j+4)^{th}$ one;

the first, second, third and fourth pads are placed at the same position in a width direction perpendicular to a carrying direction of the plurality of parts;

the first unit includes one servo motor for rotating the first pad and another servo motor for rotating the third pad, and does not include three or more servo motors, wherein the first pad and the third pad rotate about a common axis; and the second unit includes one servo motor for rotating the second pad and another servo motor for rotating the fourth pad, and does not include three or more servo motors, wherein the second pad and the fourth pad rotate about a common axis.

7. A placement method using the placement device according to claim 6 for placing the plurality of parts on the base material, wherein:

the base transfer device performs a step of transferring the base material;

the part transfer unit performs a step of transferring the plurality of parts;

the first pad repeats a step of picking up the $(i+1)^{th}$ part (i is 0 or a multiple of 4), accelerating until placing the $(i+1)^{th}$ part on the base material, and decelerating after the placement of the $(i+1)^{th}$ part;

the second pad repeats a step of picking up the $(j+2)^{th}$ part (j is 0 or a multiple of 4), accelerating until placing the $(j+2)^{th}$ part on the base material, and decelerating after the placement of the $(j+2)^{th}$ part;

the third pad repeats a step of picking up the $(i+3)^{th}$ part, accelerating until placing the $(i+3)^{th}$ part on the base material, and decelerating after the placement of the $(i+3)^{th}$ part;

the fourth pad repeats a step of picking up the $(j+4)^{th}$ part, accelerating until placing the $(j+4)^{th}$ part on the base material, and decelerating after the placement of the $(j+4)^{th}$ part; and as a result of the first, second, third and fourth pads repeating their steps, the first, second, third and fourth pads repeatedly place the $(i+1)^{th}$, $(j+2)^{th}$, $(i+3)^{th}$ and $(j+4)^{th}$ parts on the base material in the order of the $(i+1)^{th}$, $(j+2)^{th}$, $(i+3)^{th}$ and $(j+4)^{th}$ parts, so that each product has one of the $(i+1)^{th}$, $(j+2)^{th}$, $(i+3)^{th}$ and $(j+4)^{th}$ parts placed thereon.

8. A placement system comprising a pair of the placement devices according to claim 6, wherein:

a placement device, which is one of the placement devices, and a placement device, which is another one of the placement devices, are arranged so as to be spaced apart from each other in a width direction of the base material perpendicular to a carrying direction thereof so that the plurality of parts are capable of being placed on a first edge portion and a second edge portion, with respect to the width direction, of the base material.

9. A placement method using the placement device according to claim 6, wherein:

each of the first, second, third and fourth pads picks up ones of the plurality of parts and places the ones on the base material with an interval between the ones, the interval accounting for a number of positions where other parts of the plurality of parts are supposed to be placed, and the number of the other parts being one less than the total number of the pads.

* * * * *